United States Patent [19]

Glöckner et al.

[11] Patent Number: 5,052,221

[45] Date of Patent: Oct. 1, 1991

[54] METHOD FOR PREPARING PAPER FOR STRESS-STRAIN CHARACTERISTIC DETERMINATION

[75] Inventors: Erhard H. Glöckner, Eibelstadt; Hans B. Pfister, Würzburg, both of Fed. Rep. of Germany

[73] Assignee: Koenig & Bauer Aktiengesellschaft, Wurzburg, Fed. Rep. of Germany

[21] Appl. No.: 533,514

[22] Filed: Jun. 5, 1990

[30] Foreign Application Priority Data

Jun. 20, 1989 [DE] Fed. Rep. of Germany ....... 3920101

[51] Int. Cl.$^5$ ................................................ G01L 5/04
[52] U.S. Cl. ................................................... 73/159
[58] Field of Search ................. 73/866, 863, 159, 826, 73/789

[56] References Cited

FOREIGN PATENT DOCUMENTS 147419 10/1979 German Democratic Rep. .
1406478 6/1988 U.S.S.R. ................................. 73/159

OTHER PUBLICATIONS

Craver, J. Kenneth, et al., Pulp and Paper Magazine of Canada; "Sonic Velocity Response of Wet Strength Paper"; Jul. 1966; pp. T 331–T 336.

Hardacker, K. W. J. Phys. E: Sci. Instrum., vol. 14, 1981; "Instrument and Specimen Shape for Biaxial Testing of Paper".

*Primary Examiner*—Robert Raevis
*Attorney, Agent, or Firm*—Jones, Tullar & Cooper

[57] ABSTRACT

A method for preparing paper samples for determination of physical characteristics includes immersing the samples in a water-solvent mixture and then allowing the solvent to evaporate. The paper samples are thereby provided with a particular water or dampness content and can then immediately be subjected to testing on a tension testing machine or similar device.

2 Claims, No Drawings

METHOD FOR PREPARING PAPER FOR STRESS-STRAIN CHARACTERISTIC DETERMINATION

FIELD OF THE INVENTION

The present invention is directed generally to a method for preparing a paper sample for stress-strain characteristic determination. More specifically, the present invention is directed to a method for preparing paper strips for use in measurement of a stress-strain characteristic curve. Most particularly, the present invention is directed to a method for preparing paper strips for measurements of stress-strain characteristics by placing the strips in a water-solvent mixture. The paper strips are placed in the water-solvent mixture for a set period of time, are then removed from the mixture and allowed to dry for a specific length of time, and are then subjected to suitable stress-strain analysis. By using a suitable solvent-water mixture, the paper is not damaged and the measurements can be carried out in an accurate manner.

DESCRIPTION OF THE PRIOR ART

In web fed rotary printing machines, a web of paper is subjected to a number of various conditions. It is very important to have a knowledge of the physical characteristics of the paper web being sent through the web-fed rotary printing machine so that various components of the printing machine can be properly adjusted. One of the physical characteristics which is of particular interest is a knowledge of the stress-strain characteristic curve of the paper web. In flexographic printing, and especially during offset printing, water is repeatedly applied to the moving web. In a typical offset printing process this water or similar damping fluid may be applied to the web up to eight times during the passage of the paper web through the printing units. The mechanical properties of the paper web change as the surface of the web is contacted with this water or other damping fluid. The stress-strain characteristic curve of the paper being used will vary in accordance with the physical characteristics of the paper in the web being printed. The changes in the stressstrain characteristic curve of the paper web with changing physical characteristics of the particular paper being printed will effect the way in which the paper web is to be run through the printing machine.

In the past, it has been difficult to obtain reproduceable data about the influence of water dampness on the mechanical characteristics of a paper web. These measurements could only be obtained by using a climatic chamber. Strips of paper, whose characteristics were to be ascertained, were formed having specified lengths and widths. These strips of paper were placed in a climatic chamber for a period of time, and were then placed in a tension testing machine and the tear diagram, or stress-strain diagram was charted. Fast, reproduceable measurements of paper strips that had not been placed in a climatic chamber were practically impossible to obtain. This is because the dampness contents of the paper strips varied widely and this produced inaccurate and non-reproduceable results.

It will thus be apparent that there is a need for a method which will allow paper to be prepared for accurate, reproduceable measurements of physical characteristics, such as a stress-strain curve. As will be discussed subsequently, the method for preparing paper in accordance with the present invention provides for such measurements and is a substantial advance over prior art methods.

SUMMARY OF THE INVENTION

It is an object of the present invention to provide a method for preparing paper for measurement of physical characteristics.

Another object of the present invention is to provide a method for preparing paper samples for measurement of stress-strain characteristics.

A further object of the present invention is to provide a method for preparing paper samples for accurate, reproduceable stress-strain measurements.

Yet another object of the present invention is to provide a method for quickly preparing paper samples for measurements of stress-strain characteristics.

As will be discussed in detail in the description of the preferred embodiment which is set forth subsequently, the method for preparing paper for stress-strain characteristic determination in accordance with the present invention includes placing paper measuring strips in a non-emulsified solvent-water mixture for a specified period of time, removing the wetted measuring strips from the solvent-water mixture, and allowing the measuring strips to dry for a time period sufficient to allow the solvent to completely, or nearly completely evaporate. The resulting measuring strips, whose dampness is now accurately established, may then be inserted into a tension testing machine so that the stress-strain curve of the sample may be accurately obtained and charted.

It is a particular advantage of the method for preparing paper in accordance with the present invention that the paper strips to be measured can be quickly and simply brought to a pre-selectable dampness content. This allows the stress-strain relationships of the paper measuring strips to be measured under essentially equal conditions from one strip or sample to the next. These measurements do not need to be carried out in a climatic chamber or on paper strips that have been held for a lengthy period of time in such a chamber. This allows the samples to be prepared for measurement in a short period of time while not sacrificing accuracy or reproduceability.

The method for preparing paper measuring strips in accordance with the present invention allows low dampness content measuring strips to be brought to a higher dampness level. It allows paper measuring strips that have a higher moisture content to be brought down to a lower moisture content which is equal to the water percentage share in the solvent-water mixture. Thus the water dampness content of the paper can be either increased or decreased to bring it to the water percentage share in the solvent-water mixture. By selection of an appropriate solvent in the watersolvent mixture, the cellulose fibers that form the paper web are not split. Similarly, the organic salts are not dissolved from the paper.

DESCRIPTION OF THE PREFERRED EMBODIMENT

In accordance with the present invention, paper measuring strips of a uniform length and width are cut from the paper web or sheet whose physical characteristics are to be ascertained. The specific size of these measuring strips is not particularly significant so long as the measuring strips will fit in the testing machine being used and are of a uniform, reproduceable shape. Thus, paper strips having, for example a length of generally about 18 cm and a width of generally about 1 cm are typically suitable for use.

The paper measuring strips, which have been cut from the paper web or sheet whose stress-strain characteristics are to be determined, are soaked in a homogenous, non-emulsified solvent-water mixture whose concentration is accurately controlled. The paper strips preferably will be placed in the solvent-water mixture for a period of time sufficient to allow the paper to become fully saturated with the fluid. The water-solvent mixture may be made by using a number of solvents. The following solvents are particularly suitable for use in the solvent water mixture: acetone, propargyl aldehyde, formaldehyde dimethyl acetal, acetic acid methyl ester, cyclopropane oxide, ethyl propyl ether, dimethyl propanal, glyoxal, methyl isonitrile.

In the method for preparing paper in accordance with the present invention, a water-solvent mixture is first prepared by mixing one of the solvents set forth above with water to form a water-solvent mixture having a water percentage by mass which is desired to be imparted to the paper measuring strips. In the following discussion, acetone will be understood to be representative of the various solvents set forth above. An acetone-water mixture in the proportion of up to generally about a water share of 15 percent by mass may be made. Such an acetone-water mixture may easily be made using a finely graduated pipette that is exact up to 0.01 ml. The acetone-water mixture is placed in a suitable container and one or more of the paper measuring strips formed from the paper web or sheet are put into the solvent water mixture. These measuring strips should be completely immersed in the mixture. The container or receptacle is then covered and the measuring strips are allowed to absorb the watersolvent mixture for a first specific period of time. After this specifically determined residence time, such as, for example, 20 seconds, in the water-solvent mixture, the paper measuring strips are removed from the bath. Any superfluous fluid is removed from the paper strips and the strips are allowed to air dry for a second specific period of time, such as, for example 25 seconds. This period of time should be sufficient to allow virtually all of the solvent which may have been absorbed into the paper strip with the water to evaporate completely. The measuring strips are now immediately placed in a tension testing machine and the tensionstrain testing is started. The data provided can then be charted to provide a stress-strain curve which can then be evaluated.

In the method for preparing paper for determining characteristics in accordance with the present invention, the period of residence time of the paper measuring strips in the atmosphere of the measuring room at, for example, room temperature is, as was discussed above, sufficient to allow essentially all of the solvent to completely evaporate. This allows a uniform dampness, which corresponds to the water percentage in the original solvent-water mixture, to remain in the paper measuring strips. By controlling the water percentage in the water-solvent mixture, the dampness percentage in the paper measuring strips may likewise be controlled. It has been found that a particularly useful range is a water percentage of generally between about 4 and 15 percent of water in the water solvent mixture. This range allows the various solvents and water to be combined to form a mixture that does not result in the creation of an emulsion.

A number of solvents were set forth previously as being useable in the present invention to prepare the water-solvent mixture into which the paper measuring strips are immersed. While these listed solvents are particularly suited for use, they are not the only ones which may be used. Basically, all solvents are suitable for use in the preparation of the water-solvent mixture so long as their boiling points are at least 30° centigrade lower than that of water and so long as at least about 4 percent of water can be dissolved in the solvent while not forming an emulsion at the desired water content, and further so long as the solvent does not attach the cellulose fibers of the paper and does not significantly dissolve the inorganic compounds of the paper. So long as a particular solvent satisfies these criteria, it may be used to form a water-solvent mixture for use in the method for preparing paper for physical characteristics determination in accordance with the present invention.

While a preferred embodiment of a method for preparing papers for physical characteristic determination in accordance with the present invention has been set forth fully and completely hereinabove, it will be apparent to one of skill in the art that a number of changes in, for example, the particular shape of the paper measuring strips, the type of vessel used to hold the measuring strips, the type of tension measuring machine and the like may be made without departing from the true spirit and scope of the invention which is accordingly to be limited only by the following claims.

What is claimed is:

1. A method for preparing a paper sample for determination of a physical characteristic, said method including the steps of:

preparing a solvent-water mixture in which said solvent has a boiling point which is at least 30° centigrade lower than that of water and in which said solvent-water mixture is in a nonemulsified state;

placing a paper sample in said solvent-water mixture for a first time period sufficient to allow said paper sample to become saturated with said solvent-water mixture;

removing said paper sample from said solvent-water mixture; and allowing said solvent to evaporate from said paper sample for a second period of time.

2. The method of claim 1 further including the step of selecting said solvent from the group consisting of acetone, propargyl aldehyde, formaldehyde dimethyl acetal, acetic acid methyl ester, cyclopropan oxide, ethyl propyl ether, dimethyl propanal, glyoxal, and methyl isonitrile.

* * * * *